United States Patent
Tung et al.

(10) Patent No.: US 6,235,950 B1
(45) Date of Patent: May 22, 2001

(54) METHOD OF MAKING HYDROFLUOROCARBONS

(75) Inventors: Hsueh S. Tung, Getzville, NY (US); Robert S. Wedinger, Clarence, NJ (US)

(73) Assignee: Honeywell International, Morristown, NJ (US)

( * ) Notice: Subject to any disclaimer, the term of this patent is extended or adjusted under 35 U.S.C. 154(b) by 0 days.

(21) Appl. No.: 09/470,231

(22) Filed: Dec. 22, 1999

(51) Int. Cl.$^7$ .................................................. C07C 19/08
(52) U.S. Cl. ................................................... 570/142
(58) Field of Search ............................................. 570/142

(56) References Cited

U.S. PATENT DOCUMENTS

| | | | |
|---|---|---|---|
| 3,914,265 | * 10/1975 | Middleton | 570/142 |
| 4,143,078 | * 3/1979 | Gibbs | 570/142 |
| 5,399,795 | 3/1995 | Franz et al. | 570/165 |
| 5,780,691 | 7/1998 | Tung et al. | 570/134 |

FOREIGN PATENT DOCUMENTS 0539989   5/1993   (EP) .

* cited by examiner

*Primary Examiner*—Alan Siegel
(74) *Attorney, Agent, or Firm*—Colleen D. Szuch

(57) ABSTRACT

A method of producing hydrofluorocarbons and methods of producing other commercially attractive compounds formed as by-products of hydrofluorocarbon production by using ketones as a principal reactant.

21 Claims, No Drawings

METHOD OF MAKING HYDROFLUOROCARBONS

FIELD OF THE INVENTION

The present invention relates to new methods for making hydrofluorocarbons (HFCs).

BACKGROUND OF THE INVENTION

HFCs are of particular interest as potential replacements for highly useful, yet environmentally undesirable, chlorofluorocarbons (CFCs) and hydrochlorofluorocarbons (HCFCs). Unlike CFCs and HCFCs, HFCs do not contain chlorine and therefore do not decompose to form chlorine-containing chemical species, which are suspected of causing depletion of the ozone layer. While HFCs thus avoid the main disadvantage of such chlorine-containing compounds, they nevertheless possess many of the beneficial properties of those compounds. For example, HFCs have been used successfully in place of HCFCs and CFCs as heat transfer agents, blowing agents, and propellants. Thus, HFCs are desirable targets of chemical synthesis.

Unfortunately, known methods for forming HFCs generally use as starting materials highly-halogenated alkanes and alkenes, such as, for example, hexafluoropropene, hexafluoropropane and 2-chloroheptafluoropropene. For example, U.S. Pat. No. 5,399,795—Franz et al discloses a method of making 1,1,1,2,3,3,3-heptafluoropropane (HFC-227ea) in which hexafluoropropene is used as the starting material and is reacted with hydrogen fluoride (HF) to form the desired HFC. U.S. Pat. No. 5,780,6791, Tung et al. discloses a process which uses hexafluoropropane as a starting material to form HFC-227ea.

The present inventors have come to appreciate that such prior processes are disadvantageous for several reasons. One such disadvantage is that highly-halogenated compounds, when used as starting materials, tend to be very expensive. For example, hexafluoropropane at present costs about $6.00 per pound. Another disadvantage is that these prior art processes are not flexible and produce only HFC-227ea as a sole product. No useful intermediates or by-products are co-produced. Thus, the HFC-227ea produced by the prior art processes have relatively high operating costs, as well as relatively high capital costs.

Recognizing these and other drawbacks of the prior art, the present inventors have perceived a need for a new, efficient and more desirable method for producing a wide range of HFCs. These and other objects are achieved by the present invention as described below.

DESCRIPTION OF THE INVENTION AND PREFERRED EMBODIMENTS

The present invention is directed to a method of producing hydrofluorocarbons (HFCs) and to methods of producing other commercially attractive compounds which are produced as by-products of the inventive process. An important aspect of the invention is the discovery that HFCs can be advantageously produced using ketones as a principal reactant. Although it is contemplated that ketones in general will provide the advantages of the present invention, particularly preferred ketones are illustrated in Formula I below:

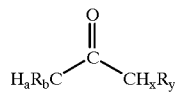

(I)

wherein, a+b3; x+y=3; and $R_b$ and $R_y$ are halogens or other chemical moieties replaceable by chlorine such as, for example, hydroxyl, sulfhydryl, or alkoxy groups.

A large number of ketones in accordance with Formula I are commercially available, including, for example, acetone. Furthermore, many compounds of Formula I are known in the literature and are obtainable by art-recognized procedures.

Applicants have discovered that ketones as a class of compounds can be used with great advantage in a process which comprises converting the ketone, and preferably a ketone in accordance with Formula I, to a hydrofluorocarbon. Applicants have discovered that a process which utilizes such a conversion operation is highly advantageous in at least two respects. First, the cost of producing HFC's according to the present ketone conversion operation is greatly reduced relative to conventional HFC production techniques. Second, the preferred form of the present ketone conversion process can be adapted to also produce valuable by-products that enhance the overall desirability of the process.

According to preferred embodiments of the present invention, the step of converting the ketone to an HFC comprises the steps of: (a) chlorinating the ketone, preferably acetone, to produce a chlorinated ketone; and (b) converting said chlorinated ketone to an HFC. Preferably the chlorinating step produces a highly chlorinated ketone, and even more preferably a fully chlorinated ketone, that is, a perchlorinated ketone. As used herein, the term "highly-chlorinated ketone" refers generally to a ketone in which the carbon chain(s) surrounding the ketone functionality are at least 80% chlorinated, wherein the percentage refers to the relative degree of chlorination, with 100% being per chlorination.

Although applicants do not wish to be bound by or to any particular theory of operation, it is believed that the methods according to the preferred aspects of the present invention involve the reaction steps shown below.

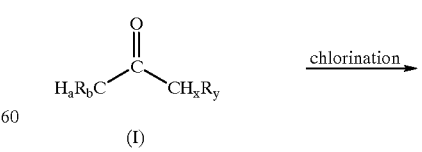

(I)

$a + b = 3, x + y = 3$
Each R is independently
selected from the group of
halogens or other moieties
replaceable by chlorine.

-continued

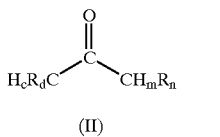

(II)

$c + d = 3, m + n = 3$
wherein $c$ is less than or equal to $a$,
$m$ is less than or equal to $x$ and each
R is independently selected from the
group of halogens or other moieties
replaceable by chlorine, provided that
formula II has at least one more chlorine
R group than formula I.

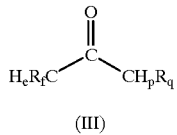

(III)

$e + f = 3, p + q = 3$,
wherein $e$ is less than or equal to $c$, $p$ is
less than or equal to $m$ and each R is
independently selected from the group of
halogens or other moieties replaceable by
chlorine, provided that at least one chlorine
group of Formula II has been replaced
by a flourine group.

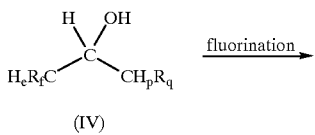 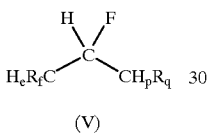

(IV) (V)

The ketone chlorination step preferably comprises reacting the ketone with a chlorinating agent under conditions effective to achieve chlorination of at least a portion of the ketone in the reactant stream, and preferably a substantial portion of the ketone in the reactant stream. It is contemplated that, in view of the teachings contained herein, those skilled in the art will be able to readily select suitable chlorinating agents for use with any particular ketone or mixture of ketones as well as the conditions effective for obtaining the desired results. In general, a suitable chlorinating agent is any material capable of providing chlorine in the reaction. A preferred chlorinating agent comprises elemental chlorine.

Those skilled in the art will appreciate that the amount of chlorinating agent to be used according to the present process will depend on many variables, including the particular ketone being chlorinated, the degree of chlorination desired and the desired yield from the chlorination reaction. Preferably, the amount of chlorinating agent used is an amount effective to achieve a greater than 90% conversion of the ketone starting material to fully-chlorinated ketone. For preferred processes in which the ketone is acetone, the mole ratio of ketone starting material to elemental chlorine is preferably from about 1:3 to about 1:12, more preferably from about 1:4 to about 1:10, and even more preferably from about 1:6 to about 1:8.

According to preferred embodiments of the present process, the ketone is reacted with a chlorinating agent to produce a stream comprising chlorinated ketones. In such embodiments, one or more reactant streams comprising a ketone and a chlorinating agent are reacted to produce a stream containing chlorinated ketones. The reactants can be fed individually or as a mixture to a chlorination reactor, or diluted with inert material, such as nitrogen or argon, or perchlorinated material. Once the reaction is under way, the reactants may be continuously added under pressure to supply the additional amounts of reactants needed to continue the process.

As desired, one or more of the reactants comprising the chlorination agent and the ketone may be preheated in at least one vaporizer before being feed to the reactor. The term "preheating" refers to vaporizing and optionally superheating the reactants. Suitable temperatures for preheating range from about 30° C. to about 200° C., preferably from about 50° C. to about 100° C. The vaporizer, as well as other vessels used in this process, may be made of any suitable corrosion resistant material.

Those skilled in the art will appreciate that the conditions under which the chlorination reaction occurs, including the pressure, temperature and period of reaction, will depend on numerous factors, including the particular starting materials used and the HFCs which are desired. In view of the teachings contained herein, those skilled in the art will be able to select the appropriate reaction conditions to achieve the particular desired result. For preferred embodiments in which the ketone reactant is acetone, the chlorination reaction is preferably carried out at temperatures of from about 50° C. to about 400° C., more preferably from about 80° C. to about 250° C., and even more preferably from about 100° C. to about 200° C. Reaction pressure is not believed to be critical, but the reaction preferably takes place in superatmospheric pressures.

In many embodiments, the chlorinated ketone stream produced in the chlorination reaction will comprise not only the chlorinated ketones, but also by-products and impurities. As an optional step, the ketones which have been chlorinated to the desired extent may be separated from this stream by conventional means, such as distillation. Optionally, but preferably, ketones that have not been chlorinated to the desired extent and/or unreacted starting material recovered from such a separation step are recycled to the reactor for further reaction. Recycling such under-chlorinated ketones and unreacted starting material generally results in higher overall yields and selectivity of the desired chlorination reaction.

As mentioned above, the present invention also preferably comprises the step of converting the chlorinated ketone to an HFC. This chlorinated ketone conversion step preferably comprises the steps of: (i) fluorinating the chlorinated ketone to form a fluorinated ketone; and (ii) converting said fluorinated ketone to an HFC. Preferably, the fluorinating step produces a highly fluorinated ketone, and even more preferably a fully-fluorinated ketone, that is, a substantially per-fluorinated ketone. The term "highly-fluorinated ketone" refers to a ketone in which the carbon chain(s) surrounding ketone functionality are at least 90% fluorinated, wherein the percentage refers to the degree of fluorination, with 100% being per-fluorination. The fluorination step preferably comprises reacting the chlorinated ketone with a fluorinating agent in the presence of a fluorination catalyst. In preferred embodiment, the fluorination reaction is carried out in a reactor vessel to produce a fluorinated ketone stream.

In general, suitable fluorination agents includes any material capable of providing fluorine to the reaction. A preferred fluorination agent is substantially anhydrous hydrogen fluoride (HF). Anhydrous hydrogen fluoride is preferred because the presence of water in the reaction tends to deactivate the fluorination catalyst. The term "substantially anhydrous", as used herein, means that the HF contains less than about 0.05 weight percent water and preferably contains less than about 0.02 weight percent water. It should be understood, however, that the presence of water in the catalyst can be compensated for by increasing the amount of catalyst used.

Preferably, the amount of fluorinating agent used is an amount effective to achieve a greater than 90% conversion of chlorinated ketone to fluorinated ketone. For embodiments in which the ketone comprises acetone, the mole ratio of chlorinated ketone to HF is preferably from about 1:6, preferably from about 1:10, and more preferably from about 1:20.

As desired, one or more of the reactants comprising the fluorination agent and the chlorinated ketone may be preheated in at least one vaporizer before feeding the reactor. Suitable temperatures for preheating range from about 125° C. to about 400° C., preferably from about 150° C. to about 350° C., and more preferably from about 175° C. to about 275° C.

The fluorination reactor is charged preferably with a fluorination catalyst before feeding the reactants to the reactor. The fluorination catalyst preferably comprised an inorganic metal catalyst which promotes a reaction involving the substitution of fluorine for chlorine in a chlorinated organic molecule. Numerous fluorination catalysts are known to those skilled in the art. Exemplary catalysts include, without limitation, chromium, copper, aluminum, cobalt, magnesium, manganese, zinc, nickel and iron oxides, hydroxides, halides, oxyhalides and inorganic salts thereof, $Cr_2O_3/Al_2O_3$, $Cr_2O_3/AlF_3$, $Cr_2O_3/carbon$, $CoCl_2CrO_3/Al_2O_3$, $NiCl_2/Cr_2O_3/Al_2O_3$, $CoCl_2AlF_3$ and $NiCl_2/AlF_3$. Additionally, supported metal catalysts such as nickel, cobalt, zinc, iron, and copper supported on chromia, magnesia, or alumina may be used. Such chromium oxide/aluminum oxide catalysts are known and are described, for example, in U.S. Pat. No. 5,155,082, which is incorporated herein by reference. Preferably, chromium oxide, a commercially available catalyst, is used.

Before adding the reactants to the fluorination reactor, it may be preferable to pretreat the catalyst chemically and/or physically to create active sites which facilitate fluorination. For example, the catalyst can be pretreated by calcining it under a flow of inert gas, such as nitrogen, at a temperature comparable to or higher than that of the fluorination reaction. Next, the calcined catalyst is exposed to a fluorinating agent alone or in combination with up to about 5 to about 99 weight percent of inert gas at a temperature from about 25° C. to about 450° C. for at least about an hour.

The reactants can be fed individually or as a mixture to the reactor, or diluted with inert material, such as nitrogen or argon, or perhalogenated material. Once the reaction is underway, the reactants may be continuously added under pressure to supply the additional amounts of reactants needed to continue the process.

The temperature at which the fluorination reaction is conducted and the period of reaction will depend on the starting materials, amounts used, and catalyst used. In view of the present teachings, those skilled in the art will be able to adapt the reaction parameters to achieve the particular desired results for numerous starting materials and desired HFCs. For methods involving the use of acetone as the starting reactant, temperatures in the fluorination reactor are preferably from about 125° C. and about 425° C., more preferably from about 200° C. to about 375° C., and even more preferably from about 275° C. and about 350° C. Pressure is not critical. Atmospheric, sub- or super-atmospheric pressures can be used.

In many embodiments, the fluorinated ketone stream produced in the fluorination reaction will comprise not only fluorinated ketones, but also by-products and impurities. As an optional step, at least a portion of the fully-fluorinated ketone may be separated from the fluorinated ketone stream via conventional purification means, such as distillation. As a further optional step, any ketone recovered from the fluorinated ketone stream may be recycled back to the reactor for further fluorination.

The preferred methods of the present invention also comprise converting fully-fluorinated ketone to HFC. While applicants contemplate that the teachings contained herein will enable those skilled in the art to adapt various fluorinated ketone conversion techniques for use with the present invention, it is preferred that conversion of the fluorinated ketone to an HFC comprises the steps of: (a) reducing the fluorinated ketone to an alcohol; and (b) converting the alcohol to an HFC.

In a preferred embodiment, the reduction step of the present invention comprises reacting of the fluorinated ketone with hydrogen in the presence of a catalyst to reduce the carbonyl of the fluorinated ketone to produce the corresponding fluorinated alcohol. In a preferred embodiment, the reduction reaction is carried out in a reactor vessel to produce a stream containing the fluorinated alcohol. In general, suitable sources of hydrogen for the reduction reaction include any material capable of providing hydrogen to the reaction. A preferred source of hydrogen is elemental hydrogen.

Preferably, the amount of hydrogen used is an amount effective to achieve a greater than 90% conversion of the fluorinated ketone, including any recycled ketone, to the corresponding alcohol. For embodiments in which the starting ketone comprises acetone, the mole ratio of fluorinated ketone to hydrogen is preferably about 1:10 or greater, more preferably about 1:5 or greater, and even more preferably about 1:2.

The reduction reactor is charged preferably with a reduction catalyst before feeding the reactants to the reactor. The term "reduction catalyst" as used herein refers to an inorganic metal catalyst which promotes a reaction involving the conversion of a ketone to an alcohol in an organic molecule. Such reduction catalysts include, for example, oxides, hydroxides, halides, oxyhalides and inorganic salts of metals, not limited to, platinum, palladium, nickel, and ruthenium. Additionally, supported metal catalysts such as palladium supported on carbon (Pd/C) can be used. Preferably, Pd/C catalyst is used.

As desired, the fluorinated ketone may be preheated in at least one vaporizer before feeding same to the reduction reactor. Suitable temperatures for preheating range from about 25° C. to about 400° C. , preferably from about 100° C. to about 200° C.

The temperature and pressure at which the reaction is conducted and the period of reaction will depend on the starting materials and amounts used. In view of the present teachings, those skilled in the art will be able to adapt the reaction parameters to achieve the particular desired results for numerous starting materials and desired HFCs. For methods involving the use of acetone as the starting reactant, temperatures in the reduction reactor are preferably from about 25° C. to about 400° C., more preferably from about 50° C. to about 300° C., and even more preferably from about 100° C. and about 200° C. For such embodiments, the reactor pressure is preferably from about 0 psig to about 1000 psig, more preferably from about 50 psig to about 500 psig, and still more preferably from about 100 psig to about 200 psig.

As mentioned above, the preferred methods of the present invention comprise converting the fluorinated alcohol to the desired HFC. While applicants contemplate that the teachings contained herein will enable those skilled in the art to adapt various known techniques for fluorinating an alcohol for use in accordance with the present invention, it is preferred that the alcohol conversion step comprises reacting the highly-fluorinated alcohol with a fluorinating agent. A suitable fluorination agent includes any material capable of providing fluorine in the reaction. A preferred fluorination agent includes, for example, elemental fluorine.

Preferably, the amount of fluorinating agent used is an amount effective to achieve a greater than 90% conversion of the highly-fluorinated alcohol to HFC. For embodiments in which the starting ketone comprises acetone and the fluorinating agent is elemental fluorine, the mole ratio of fluorinated alcohol to $F_2$ is preferably from about 1:0.01 to about 1:0.15, and even more preferably about 1:0.05.

More preferably, the fluorination of the alcohol is conducted in the presence of an inert diluent, such as nitrogen, argon, helium or a perfluorinated organic compound.

As desired, one or more of the reactants comprising the fluorination agent and the alcohol may be preheated in at least one vaporizer before feeding the reactor. Suitable temperatures for preheating range from about 25° C. to about 200° C., preferably from about 50° C. to about 150° C., and more preferably from about 75° C. to about 100° C.

The fluorination reactor is packed preferably with an inert or a catalytical material to provide reaction with large surface area, such a a nickel mesh.

As desired, this reaction may run at sub-ambient temperature to remove large amounts of heat generated from this reaction.

Products produced in accordance with the present invention find particular utility as replacements for fluorocarbons, chlorofluorocarbons and hydrochlorofluorocarbons in a wide variety of applications. For example, the products of the present invention can be used as aerosols, refrigerants, blowing agents, and fire-extinguisher compounds.

EXAMPLE 1

In order to illustrate, in an non-limiting manner, the present invention is described in connection with the following example, which describes the preparation of 1,1,1,2,3,3,3-heptafluoropropane from acetone.

To a vapor phase plug flow reactor, 1 g/min of acetone, preheated to 200° C., is fed with 10 g/min of elemental chlorine to react at about 250° C. in an isothermal condition at atmospheric pressure. The plug flow reactor has a dimension of ½" by 3' long pipe and is made of Inconel alloy, packed with nickel mesh. An in-line gas chromatograph is equipped to take to take on-line samples periodically.

Analysis of on-line samples indicates formation of hexachloroacetone ("HCA") in about 60% single-pass selectivity as well as lesser-chlorinated acetone products including: monochloro-, dichloro-, trichloro-, tetrachloro-, and pentachloroacetone in a combined yield of about 90%. The lesser-chlorinated acetone products are separated from the hexachloroacetone via distillation and are recycled back into the vapor phase plug flow reactor for making more hexachloroacetone. The overall selectivity is about 90%.

Subsequently, 100 ml of chromium oxide ($Cr_2O_3$) catalyst is packed in a vapor phase reactor having dimensions similar to those of the aforementioned plug flow reactor. This catalyst is then heat-treated at 375° C. in 1 L/min nitrogen for 16 hours, followed by hydrogen fluoride ("HF") treatment at 350° C. for 4 hours. The HF flow rate is 1 ml/min in 250 ml/min nitrogen.

After catalyst pre-treatment is completed, 43 g/hr HCA and 45 g/hr anhydrous HF is fed to the reactor. The reaction is conducted at atmospheric pressure and at two different temperatures, 300° C. and 325° C. The contact time is about 5 seconds and the mole ratio of HF/HCA is about 14.

The selectivity and productivity of the above reaction at both 300° C. and 325° C. are measured using an in-line gas chromatography, and the results are listed in Table 1. As used herein, the term "selectivity" refers generally to the mole percent of the limiting reactant converted to a given product. Also, as used herein, "productivity" is defined as the weight of a desired product formed in one hour per unit volume of catalyst used in the reaction.

As shown in Table 1, the overall conversion of HCA is greater than 99%, the single pass selectivity for hexafluoroacetone ("6FK") is greater than 58% and lesser-fluorinated acetone products ("1FK-5FK") including: monofluoro-, difluoro-, trifluoro-, tetrafluoro- and pentafluoroacetone are formed with a combined selectivity of about 19–26%. The total combined selectivity is greater than 77% at 325° C. and approximately 90% at 300° C.

Furthermore, the productivity of the reaction, as measured in the standard units of lbs./hr/ft³, is 15.0 lbs./hr/ft³ at 300° C. and 12.9 lbs./hr/ft³ at 325° C. The flow rate units, g/hr, and volume of catalyst units, cc, were So converted to conform with standard practice in the art.

The lesser-fluorinated acetone products are separated from the hexafluoroacetone via distillation. The lesser-fluorinated acetone products are recycled back into the reactor to produce more hexafluoroacetone.

As further indicated by Table I, other halogenated by-products are formed in the fluorination reaction. These include, for example, one-carbon compounds of the formula: $COF_2$ and $CClF_3$ ("13"); and a mixture of fully-halogenated, two-carbon chlorofluorocarbons having from 3–6 fluorine substituents thereon ("110's").

TABLE I

Fluorination of Hexachloroacetone - Selectivity and Productivity

| Reaction Product | Selectivity at 300° C. (%) | Selectivity at 325° C. (%) | Productivity at 300° C. (lbs/hr/ft³) | Productivity at 325° C. (lbs/hr/ft³) |
|---|---|---|---|---|
| 6 FK | 64.0 | 58.2 | 15.0 | 12.9 |
| 1 FK–5 FK | 25.7 | 19.0 | — | — |
| Combined fluorinated ketones | 89.7 | 77.2 | — | — |
| 13 | 0.4 | 0.8 | — | — |
| $COF_2$ | trace | trace | — | — |
| 110's | 5.4 | 17.5 | — | — |
| unknown | 4.5 | 4.5 | — | — |
| Conversion HCA | 99.6 | 99.6 | — | — |

Approximately 100cc of Pd/C catalyst is packed into a ½" diameter pipe reactor. Approximately 1 g/min of the hexafluoroacetone and 500cc/min hydrogen gas is fed into the reactor at atmospheric pressure and 180° C. Hexafluoro-2-propanol is produced in greater than 90% yield.

A vapor plug flow reactor ½" diameter×3' long Monel® pipe is fed with 1 g/min of the hexafluoro-2-propanol and 150 cc/min of elemental fluorine at ambient conditions to produce 1,1,1,2,3,3,3 heptafluoropropane in greater than 90% yield.

What is claimed is:

1. A method for the preparation of a hydrofluorocarbon comprising the steps of:

(a) chlorinating a ketone by reacting the ketone with elemental chlorine at a temperature in the range of from about 50° C. to about 400° C. to form a chlorinated ketone;

(b) fluorinating the chlorinated ketone by reacting the chlorinated ketone with hydrofluoric acid in an amount effective to achieve at least 90% conversion at a temperature of from about 125° C. to about 400° C. in the presence of an inorganic metal catalyst to form a fluorinated ketone;

(c) reducing the fluorinated ketone to form a fluorinated alcohol by reacting the fluorinated ketone with elemental hydrogen in the presence of a reduction catalyst at a temperature of from about 25° C. to about 400° C.; and (d) fluorinating the fluorinated alcohol to form a hydrofluorocarbon by reacting the fluorinated alcohol with elemental fluorine in the presence of an inert diluent.

2. The method of claim 1, wherein the chlorination step (a) produces a product stream comprising a mixture of fully chlorinated ketone and partially chlorinated ketones.

3. The method of claim 2, further comprising the step of separating at least a portion of said partially chlorinated ketones from said product stream.

4. The method of claim 3, further comprising the step of recycling said separated portion of said partially chlorinated ketones to said chlorinating step (a).

5. The method of claim 1, wherein the fluorination step (b) produces a product stream comprising a mixture of fully fluorinated ketone and partially fluorinated ketones.

6. The method of claim 5, further comprising the step of separating at least a portion of said partially fluorinated ketones from said product stream.

7. The method of claim 6, further comprising the step of using said separated portion of said partially fluorinated ketones as a further reactant in said fluorinating step (b).

8. The method of claim 1, wherein the reduction step (c) produces a product stream comprising a mixture of partially fluorinated alcohols and fluorinated ketones.

9. The method of claim 8, further comprising the step of separating at least a portion of said fluorinated ketones from said product stream.

10. The method of claim 9, further comprising the step of using said separated portion of said fluorinated ketones as a further reactant in said reduction step (c).

11. The method of claim 1, wherein the fluorinating step (d) produces a product stream comprising a mixture of hydrofluorocarbons and fluorinated alcohols.

12. The method of claim 11, further comprising the step of separating at least a portion of said fluorinated alcohols from said product stream.

13. The method of claim 12, further comprising the step of using said separated portion of said fluorinated alcohols as a further reactant in said fluorination step (d).

14. The method of claim 1, wherein the chlorination step (a) comprises chlorinating a compound having the formula (I) as follows:

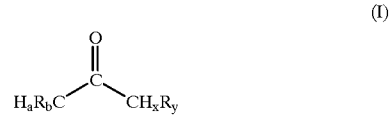

wherein a+b=3; x+y=3; and each R is independently selected from the group of halogens or other chemical moieties replaceable by chlorine.

15. The method of claim 14, wherein the chlorination step (a) comprises chlorinating a compound in which a and x are each either 0 or 1.

16. The method of claim 1 wherein the fluorination step (b) comprises fluorinating a fully chlorinated ketone to produce a fully fluorinated ketone.

17. The method of claim 16 wherein the chlorination step (a) comprises chlorinating a compound having the formula (I) follows

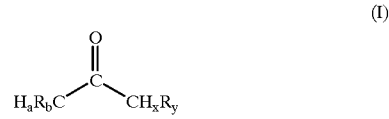

wherein a+b=3; x+y=3; and each R is selected from the group of halogens or other chemical moieties replaceable by chlorine, to produce a fully chlorinated ketone.

18. The method of claim 17, wherein the chlorination step (a) comprises chlorinating a compound in which a and x are each either 0 or 1.

19. The method of claim 18, wherein the reduction step (c) comprises reducing said fluorinated ketone to form a fluorinated $C_3$ alcohol.

20. The method of claim 19, wherein the fluorination step (d) comprises fluorinating said $C_3$ alcohol to form a $C_3$ hydrofluorocarbon.

21. The method of claim 1, wherein said hydrofluorocarbon consists essentially of 1,1,1,2,3,3,3-heptafluoropropane and, said chlorinating step (a) comprises chlorinating acetone to produce hexachloroacetone, said fluorinating step (b) comprises fluorinating said hexachloroacetone to produce hexafluoroacetone, said reducing step (c) comprises reducing said hexafluoroacetone to produce hexafluoro-2-propanol, and said fluorinating step (d) comprises fluorinating said hexafluoro-2-propanol to produce 1,1,1,2,3,3,3-heptafluoropropane.

* * * * *